United States Patent
Rosén

(10) Patent No.: US 11,282,605 B2
(45) Date of Patent: Mar. 22, 2022

(54) INTRAOCULAR LENSES THAT IMPROVE POST-SURGICAL SPECTACLE INDEPENDENT AND METHODS OF MANUFACTURING THEREOF

(71) Applicant: AMO Groningen B.V., Groningen (NL)

(72) Inventor: Robert Rosén, Groningen (NL)

(73) Assignee: AMO Groningen B.V., Groningen (NL)

( * ) Notice: Subject to any disclaimer, the term of this patent is extended or adjusted under 35 U.S.C. 154(b) by 188 days.

(21) Appl. No.: 16/205,206

(22) Filed: Nov. 29, 2018

(65) Prior Publication Data

US 2019/0164647 A1 May 30, 2019

Related U.S. Application Data

(60) Provisional application No. 62/593,162, filed on Nov. 30, 2017.

(51) Int. Cl.
| | |
|---|---|
| *G16H 50/20* | (2018.01) |
| *A61B 34/10* | (2016.01) |
| *A61F 2/16* | (2006.01) |
| *G16H 50/50* | (2018.01) |
| *G02C 7/02* | (2006.01) |

(52) U.S. Cl.
CPC ............. *G16H 50/20* (2018.01); *A61B 34/10* (2016.02); *A61F 2/16* (2013.01); *G02C 7/024* (2013.01); *G16H 50/50* (2018.01); *A61B 2034/108* (2016.02); *A61F 2240/002* (2013.01)

(58) Field of Classification Search
CPC .. A61B 34/10; A61B 3/00; A61B 3/10; A61B 3/1015; A61B 3/107; A61B 3/0025; A61B 2034/108; G16H 50/20; G16H 50/50; G16H 40/63; G16H 20/40; G16H 20/00; A61F 2/16; A61F 2/1637; A61F 2/1648; A61F 2240/002; G02C 7/024
USPC ............ 351/159.01, 159.02, 159.73, 159.74, 351/159.77, 159.8, 178, 246, 247, 200, 351/205, 206, 211, 212; 356/124, 124.5, 356/125
See application file for complete search history.

(56) References Cited

U.S. PATENT DOCUMENTS

| | | |
|---|---|---|
| 2,077,092 A | 4/1937 | Broder |
| 3,305,294 A | 2/1967 | Alvarez |

(Continued)

FOREIGN PATENT DOCUMENTS

| | | |
|---|---|---|
| DE | 3107675 U1 | 7/1981 |
| DE | 3439551 A1 | 4/1986 |

(Continued)

OTHER PUBLICATIONS

International Search Report and Written Opinion for Application No. PCT/EP2018/082950, dated Mar. 19, 2019, 12 pages.

(Continued)

*Primary Examiner* — Jie Lei
(74) *Attorney, Agent, or Firm* — Johnson & Johnson Surgical Vision, Inc.

(57) ABSTRACT

A Bayesian model for predicting spectacle independence of one or more IOLs based on pre-clinical data (e.g., visual acuity value for one or more defocus values) of an IOL. The Bayesian model is trained to assign appropriate weights for different combinations of defocus values.

9 Claims, 6 Drawing Sheets

(56) References Cited

U.S. PATENT DOCUMENTS

| | | |
|---|---|---|
| 3,367,734 A | 2/1968 | Karl |
| 3,735,685 A | 5/1973 | Plummer |
| 4,010,496 A | 3/1977 | Neefe |
| 4,056,311 A | 11/1977 | Winthrop |
| 4,077,071 A | 3/1978 | Freeman |
| 4,093,361 A | 6/1978 | Erickson et al. |
| 4,134,160 A | 1/1979 | Bayers |
| 4,162,122 A | 7/1979 | Cohen |
| 4,174,543 A | 11/1979 | Kelman |
| 4,210,391 A | 7/1980 | Cohen et al. |
| 4,249,272 A | 2/1981 | Poler |
| 4,254,509 A | 3/1981 | Tennant |
| 4,254,510 A | 3/1981 | Tennant |
| 4,316,293 A | 2/1982 | Bayers |
| 4,319,564 A | 3/1982 | Karickhoff |
| 4,338,005 A | 7/1982 | Cohen |
| 4,340,283 A | 7/1982 | Cohen |
| 4,370,760 A | 2/1983 | Kelman |
| 4,377,873 A | 3/1983 | Reichert, Jr. |
| 4,402,579 A | 9/1983 | Poler |
| 4,403,353 A | 9/1983 | Tennant |
| 4,404,694 A | 9/1983 | Kelman |
| 4,409,691 A | 10/1983 | Levy |
| 4,424,597 A | 1/1984 | Schlegel |
| 4,437,733 A | 3/1984 | Takahashi et al. |
| 4,446,581 A | 5/1984 | Blake |
| 4,480,340 A | 11/1984 | Shepard |
| 4,500,382 A | 2/1985 | Foster |
| 4,504,982 A | 3/1985 | Burk |
| 4,551,864 A | 11/1985 | Akhavi |
| 4,556,998 A | 12/1985 | Siepser |
| 4,560,383 A | 12/1985 | Leiske |
| 4,605,409 A | 8/1986 | Kelman |
| 4,605,411 A | 8/1986 | Fedorov et al. |
| 4,629,460 A | 12/1986 | Dyer |
| 4,629,462 A | 12/1986 | Feaster |
| 4,637,697 A | 1/1987 | Freeman |
| 4,642,112 A | 2/1987 | Freeman |
| 4,655,565 A | 4/1987 | Freeman |
| 4,665,913 A | 5/1987 | L'Esperance, Jr. |
| 4,669,466 A | 6/1987 | L'Esperance |
| 4,673,406 A | 6/1987 | Schlegel |
| 4,676,791 A | 6/1987 | Lemaster et al. |
| 4,676,792 A | 6/1987 | Praeger |
| 4,681,102 A | 7/1987 | Bartell |
| 4,687,484 A | 8/1987 | Kaplan |
| 4,687,485 A | 8/1987 | Lim et al. |
| RE32,525 E | 10/1987 | Pannu |
| 4,725,277 A | 2/1988 | Bissonette |
| 4,732,148 A | 3/1988 | L'Esperance, Jr. |
| 4,734,095 A | 3/1988 | Siepser |
| 4,764,930 A | 8/1988 | Bille et al. |
| 4,770,172 A | 9/1988 | L'Esperance, Jr. |
| 4,773,414 A | 9/1988 | L'Esperance, Jr. |
| 4,778,462 A | 10/1988 | Grendahl |
| 4,781,717 A | 11/1988 | Grendahl |
| 4,787,903 A | 11/1988 | Grendahl |
| 4,787,904 A | 11/1988 | Severin et al. |
| 4,795,462 A | 1/1989 | Grendahl |
| 4,798,608 A | 1/1989 | Grendahl |
| 4,798,609 A | 1/1989 | Grendahl |
| 4,828,558 A | 5/1989 | Kelman |
| 4,834,748 A | 5/1989 | McDonald |
| 4,863,261 A | 9/1989 | Flammer |
| 4,863,539 A | 9/1989 | Lee et al. |
| 4,898,461 A | 2/1990 | Portney |
| 4,932,970 A | 6/1990 | Portney |
| 4,995,714 A | 2/1991 | Cohen |
| 4,995,715 A | 2/1991 | Cohen |
| 4,997,442 A | 3/1991 | Barrett |
| 5,016,977 A | 5/1991 | Baude et al. |
| 5,019,097 A | 5/1991 | Knight et al. |
| 5,042,938 A | 8/1991 | Shimozono |
| 5,047,052 A | 9/1991 | Dubroff |
| 5,054,905 A | 10/1991 | Cohen |
| 5,056,908 A | 10/1991 | Cohen |
| 5,066,301 A | 11/1991 | Wiley |
| 5,071,432 A | 12/1991 | Baikoff |
| 5,078,742 A | 1/1992 | Dahan |
| 5,089,023 A | 2/1992 | Swanson |
| 5,096,285 A | 3/1992 | Silberman |
| 5,108,388 A | 4/1992 | Trokel et al. |
| 5,114,220 A | 5/1992 | Baude et al. |
| 5,117,306 A | 5/1992 | Cohen |
| 5,120,120 A | 6/1992 | Cohen |
| 5,121,979 A | 6/1992 | Cohen |
| 5,121,980 A | 6/1992 | Cohen |
| 5,133,749 A | 7/1992 | Nordan |
| 5,144,483 A | 9/1992 | Cohen |
| 5,147,395 A | 9/1992 | Willis |
| 5,147,397 A | 9/1992 | Christ et al. |
| 5,163,934 A | 11/1992 | Munnerlyn |
| 5,173,723 A | 12/1992 | Volk et al. |
| 5,184,405 A | 2/1993 | Cress |
| 5,197,981 A | 3/1993 | Southard |
| 5,201,763 A | 4/1993 | Brady et al. |
| 5,203,790 A | 4/1993 | McDonald |
| 5,207,668 A | 5/1993 | L'Esperance, Jr. |
| 5,217,491 A | 6/1993 | Vanderbilt |
| 5,219,343 A | 6/1993 | L'Esperance, Jr. |
| 5,225,858 A | 7/1993 | Portney |
| 5,229,797 A | 7/1993 | Futhey et al. |
| 5,258,025 A | 11/1993 | Fedorov et al. |
| 5,278,592 A | 1/1994 | Marie et al. |
| 5,379,110 A | 1/1995 | Matsui et al. |
| 5,408,281 A | 4/1995 | Zhang |
| 5,433,745 A | 7/1995 | Graham et al. |
| 5,476,513 A | 12/1995 | Brady et al. |
| 5,479,220 A | 12/1995 | Komatsu et al. |
| 5,567,365 A | 10/1996 | Weinschenk, III et al. |
| 5,571,177 A | 11/1996 | Deacon et al. |
| 5,620,720 A | 4/1997 | Glick et al. |
| 5,628,796 A | 5/1997 | Suzuki |
| 5,646,791 A | 7/1997 | Glockler |
| 5,652,638 A | 7/1997 | Roffman et al. |
| 5,652,640 A | 7/1997 | Schneider et al. |
| 5,691,800 A | 11/1997 | Iki et al. |
| 5,699,142 A | 12/1997 | Lee et al. |
| 5,716,403 A | 2/1998 | Tran et al. |
| 5,748,282 A | 5/1998 | Freeman |
| 5,760,871 A | 6/1998 | Kosoburd et al. |
| 5,796,462 A | 8/1998 | Roffman et al. |
| 5,801,807 A | 9/1998 | Satake et al. |
| 5,928,282 A | 7/1999 | Nigam |
| 5,968,094 A | 10/1999 | Werblin et al. |
| 5,993,438 A | 11/1999 | Juhasz et al. |
| 6,015,435 A | 1/2000 | Valunin et al. |
| 6,051,024 A | 4/2000 | Cumming |
| 6,126,283 A | 10/2000 | Wen et al. |
| 6,126,286 A | 10/2000 | Portney |
| 6,129,759 A | 10/2000 | Chambers |
| 6,142,625 A | 11/2000 | Sawano et al. |
| 6,179,870 B1 | 1/2001 | Sourdille et al. |
| 6,210,005 B1 | 4/2001 | Portney |
| 6,235,055 B1 | 5/2001 | Chu |
| 6,241,356 B1 | 6/2001 | Von Wallfeld et al. |
| 6,261,321 B1 | 7/2001 | Kellan |
| 6,319,282 B1 | 11/2001 | Nishi |
| 6,338,559 B1 | 1/2002 | Williams et al. |
| 6,419,697 B1 | 7/2002 | Kelman |
| 6,457,826 B1 | 10/2002 | Lett |
| 6,460,997 B1 | 10/2002 | Frey et al. |
| 6,464,355 B1 | 10/2002 | Gil |
| 6,474,814 B1 | 11/2002 | Griffin |
| 6,488,708 B2 | 12/2002 | Sarfarazi |
| 6,491,721 B2 | 12/2002 | Freeman et al. |
| 6,497,483 B2 | 12/2002 | Frey et al. |
| 6,527,389 B2 | 3/2003 | Portney |
| 6,533,416 B1 | 3/2003 | Fermigier et al. |
| 6,536,899 B1 | 3/2003 | Fiala |
| 6,537,317 B1 | 3/2003 | Steinert et al. |
| 6,547,822 B1 | 4/2003 | Lang |
| 6,550,917 B1 | 4/2003 | Neal et al. |
| 6,554,859 B1 | 4/2003 | Lang et al. |

(56) References Cited

U.S. PATENT DOCUMENTS

| | | |
|---|---|---|
| 6,557,992 B1 | 5/2003 | Dwyer et al. |
| 6,575,572 B2 | 6/2003 | Lai et al. |
| 6,598,606 B2 | 7/2003 | Terwee et al. |
| 6,609,793 B2 | 8/2003 | Norrby et al. |
| 6,705,729 B2 | 3/2004 | Piers et al. |
| 6,786,603 B2 | 9/2004 | Altmann |
| 6,802,605 B2 | 10/2004 | Cox et al. |
| 6,808,262 B2 | 10/2004 | Chapoy et al. |
| 6,817,714 B2 | 11/2004 | Altmann |
| 6,830,332 B2 | 12/2004 | Piers et al. |
| 6,846,326 B2 | 1/2005 | Zadno-Azizi et al. |
| 6,851,803 B2 | 2/2005 | Wooley et al. |
| 6,899,425 B2 | 5/2005 | Roffman et al. |
| 6,923,539 B2 | 8/2005 | Simpson et al. |
| 6,923,540 B2 | 8/2005 | Ye et al. |
| 6,986,578 B2 | 1/2006 | Jones |
| 7,036,931 B2 | 5/2006 | Lindacher et al. |
| 7,048,760 B2 | 5/2006 | Cumming |
| 7,061,693 B2 | 6/2006 | Zalevsky |
| 7,073,906 B1 | 7/2006 | Portney |
| 7,137,702 B2 | 11/2006 | Piers et al. |
| 7,156,516 B2 | 1/2007 | Morris et al. |
| 7,188,949 B2 | 3/2007 | Bandhauer et al. |
| 7,281,797 B2 | 10/2007 | Yamaguchi et al. |
| 7,287,852 B2 | 10/2007 | Fiala |
| 7,293,873 B2 | 11/2007 | Dai et al. |
| 7,296,893 B2 | 11/2007 | Dai |
| 7,339,539 B2 | 3/2008 | Joannopoulos et al. |
| 7,350,916 B2 | 4/2008 | Hong et al. |
| 7,365,917 B2 | 4/2008 | Zalevsky |
| 7,377,640 B2 | 5/2008 | Piers et al. |
| 7,425,068 B2 | 9/2008 | Koest |
| 7,441,894 B2 | 10/2008 | Zhang et al. |
| 7,455,404 B2 | 11/2008 | Bandhauer et al. |
| 7,455,407 B2 | 11/2008 | Neal et al. |
| 7,475,986 B2 | 1/2009 | Dai et al. |
| 7,547,102 B2 | 6/2009 | Dai |
| 7,615,073 B2 | 11/2009 | Deacon et al. |
| 7,616,330 B2 | 11/2009 | Neal et al. |
| 7,659,971 B2 | 2/2010 | Warden et al. |
| 7,726,813 B2 | 6/2010 | Dai |
| 7,784,946 B2 | 8/2010 | Leblanc |
| 7,794,497 B2 | 9/2010 | Brady et al. |
| 7,857,451 B2 | 12/2010 | Thibos et al. |
| 7,871,162 B2 | 1/2011 | Weeber |
| 7,911,211 B2 | 3/2011 | Crain et al. |
| 7,931,371 B2 | 4/2011 | Dai |
| 7,931,374 B2 | 4/2011 | Dai et al. |
| 7,938,538 B2 | 5/2011 | Lu et al. |
| 7,944,553 B1 | 5/2011 | Simpson et al. |
| 7,969,585 B2 | 6/2011 | Neal et al. |
| 8,123,357 B2 | 2/2012 | Dai et al. |
| 8,382,281 B2 | 2/2013 | Weeber |
| 8,480,228 B2 | 7/2013 | Weeber |
| 8,596,787 B2 | 12/2013 | Dai |
| 8,657,445 B2 | 2/2014 | Olsen |
| 8,696,119 B2 | 4/2014 | Van Der Mooren et al. |
| 8,740,382 B1 | 6/2014 | Liu et al. |
| 8,746,882 B2 | 6/2014 | Vidal et al. |
| 8,764,822 B2 | 7/2014 | Harris et al. |
| 8,862,447 B2 | 10/2014 | Weeber |
| 9,211,061 B2 | 12/2015 | Kasthurirangan et al. |
| 9,241,627 B2 | 1/2016 | Steinmueller |
| 9,393,108 B2 | 7/2016 | Canovas Vidal et al. |
| 9,491,431 B2 | 11/2016 | Zhou |
| 9,700,201 B2 | 7/2017 | Bex et al. |
| 2001/0051825 A1 | 12/2001 | Peterson |
| 2002/0118337 A1 | 8/2002 | Perrott et al. |
| 2002/0173846 A1 | 11/2002 | Blake et al. |
| 2002/0196408 A1 | 12/2002 | Bhalakia et al. |
| 2002/0196412 A1 | 12/2002 | Abitbol |
| 2003/0033013 A1 | 2/2003 | Callahan et al. |
| 2003/0053025 A1 | 3/2003 | Turner et al. |
| 2003/0076478 A1 | 4/2003 | Cox |
| 2003/0163122 A1 | 8/2003 | Sumiya |
| 2003/0171808 A1 | 9/2003 | Phillips |
| 2003/0189690 A1 | 10/2003 | Mihashi et al. |
| 2004/0021824 A1 | 2/2004 | Ye et al. |
| 2004/0021825 A1 | 2/2004 | Richardson |
| 2004/0054358 A1 | 3/2004 | Cox et al. |
| 2004/0057010 A1 | 3/2004 | Altmann |
| 2004/0068317 A1 | 4/2004 | Knight |
| 2004/0085515 A1 | 5/2004 | Roffman et al. |
| 2004/0106992 A1 | 6/2004 | Lang et al. |
| 2004/0111153 A1 | 6/2004 | Woods et al. |
| 2004/0150789 A1 | 8/2004 | Jones |
| 2004/0156014 A1 | 8/2004 | Piers et al. |
| 2004/0167622 A1 | 8/2004 | Sunalp et al. |
| 2004/0183997 A1 | 9/2004 | Suzuki |
| 2004/0230299 A1 | 11/2004 | Simpson et al. |
| 2004/0260275 A1 | 12/2004 | Liang et al. |
| 2005/0024647 A1 | 2/2005 | Montgomery |
| 2005/0096226 A1 | 5/2005 | Stock et al. |
| 2005/0122474 A1 | 6/2005 | Koretz |
| 2005/0125056 A1 | 6/2005 | Deacon et al. |
| 2005/0128432 A1 | 6/2005 | Altmann |
| 2005/0195364 A1 | 9/2005 | Dai |
| 2005/0203619 A1 | 9/2005 | Altmann |
| 2005/0251254 A1 | 11/2005 | Brady et al. |
| 2005/0267575 A1 | 12/2005 | Nguyen et al. |
| 2006/0009816 A1 | 1/2006 | Fang et al. |
| 2006/0030938 A1 | 2/2006 | Altmann |
| 2006/0034003 A1 | 2/2006 | Zalevsky |
| 2006/0055877 A1 | 3/2006 | Yanari |
| 2006/0055883 A1 | 3/2006 | Morris et al. |
| 2006/0066808 A1 | 3/2006 | Blum et al. |
| 2006/0068453 A1 | 3/2006 | Altieri |
| 2006/0098162 A1 | 5/2006 | Bandhauer et al. |
| 2006/0098163 A1 | 5/2006 | Bandhauer et al. |
| 2006/0109421 A1 | 5/2006 | Ye et al. |
| 2006/0116763 A1 | 6/2006 | Simpson |
| 2006/0116764 A1 | 6/2006 | Simpson |
| 2006/0116765 A1 | 6/2006 | Blake et al. |
| 2006/0176572 A1 | 8/2006 | Fiala |
| 2006/0203198 A1 | 9/2006 | Liang |
| 2006/0238702 A1 | 10/2006 | Glick et al. |
| 2006/0244904 A1 | 11/2006 | Hong et al. |
| 2006/0244906 A1 | 11/2006 | Piers et al. |
| 2006/0244916 A1 | 11/2006 | Guillon |
| 2006/0274268 A1 | 12/2006 | Andino et al. |
| 2006/0279699 A1 | 12/2006 | Liang |
| 2006/0279700 A1 | 12/2006 | Liang |
| 2007/0052920 A1 | 3/2007 | Stewart et al. |
| 2007/0052927 A1 | 3/2007 | Noda et al. |
| 2007/0129803 A1 | 6/2007 | Cumming et al. |
| 2007/0171362 A1 | 7/2007 | Simpson et al. |
| 2007/0182924 A1 | 8/2007 | Hong et al. |
| 2007/0195265 A1 | 8/2007 | Dreher et al. |
| 2007/0211214 A1 | 9/2007 | Dai |
| 2007/0268453 A1 | 11/2007 | Hong et al. |
| 2007/0285617 A1 | 12/2007 | Mills et al. |
| 2008/0018910 A1 | 1/2008 | Neal et al. |
| 2008/0030677 A1 | 2/2008 | Simpson |
| 2008/0033546 A1 | 2/2008 | Liang |
| 2008/0079895 A1 | 4/2008 | Jubin et al. |
| 2008/0161913 A1 | 7/2008 | Brady et al. |
| 2008/0161914 A1 | 7/2008 | Brady et al. |
| 2008/0198331 A1 | 8/2008 | Azar et al. |
| 2008/0231809 A1 | 9/2008 | Haigis |
| 2008/0269642 A1 | 10/2008 | Deacon et al. |
| 2008/0273169 A1 | 11/2008 | Blum et al. |
| 2008/0291393 A1 | 11/2008 | Menezes |
| 2009/0000628 A1 | 1/2009 | Somani et al. |
| 2009/0012609 A1 | 1/2009 | Geraghty et al. |
| 2009/0036980 A1 | 2/2009 | Norrby et al. |
| 2009/0062911 A1 | 3/2009 | Bogaert |
| 2009/0164008 A1 | 6/2009 | Hong et al. |
| 2009/0168019 A1 | 7/2009 | Tuan |
| 2009/0187242 A1 | 7/2009 | Weeber et al. |
| 2009/0210054 A1 | 8/2009 | Weeber et al. |
| 2009/0231546 A1 | 9/2009 | Dai |
| 2009/0234448 A1 | 9/2009 | Weeber et al. |
| 2009/0268155 A1 | 10/2009 | Weeber |
| 2009/0268158 A1 | 10/2009 | Weeber |

(56) References Cited

U.S. PATENT DOCUMENTS

| | | |
|---|---|---|
| 2009/0275929 A1 | 11/2009 | Zickler |
| 2009/0279048 A1 | 11/2009 | Hong et al. |
| 2009/0281552 A1 | 11/2009 | Hiramatsu et al. |
| 2009/0292354 A1 | 11/2009 | Gontijo et al. |
| 2009/0295295 A1 | 12/2009 | Shannon et al. |
| 2009/0303465 A1 | 12/2009 | Clements et al. |
| 2009/0323020 A1 | 12/2009 | Zhao et al. |
| 2010/0016961 A1 | 1/2010 | Hong et al. |
| 2010/0016965 A1 | 1/2010 | Hong et al. |
| 2010/0082017 A1 | 4/2010 | Zickler et al. |
| 2010/0097569 A1 | 4/2010 | Weeber et al. |
| 2010/0130888 A1 | 5/2010 | Deacon et al. |
| 2010/0161048 A1 | 6/2010 | Schaper, Jr. |
| 2010/0179793 A1 | 7/2010 | Chernyak et al. |
| 2010/0220185 A1 | 9/2010 | Vertoprakhov et al. |
| 2010/0234833 A1 | 9/2010 | Dai |
| 2010/0315589 A1 | 12/2010 | Portney |
| 2011/0080562 A1 | 4/2011 | Iizuka et al. |
| 2011/0149236 A1 | 6/2011 | Weeber |
| 2011/0166652 A1 | 7/2011 | Bogaert et al. |
| 2011/0205486 A1 | 8/2011 | Zhao |
| 2011/0211163 A1 | 9/2011 | Meuse et al. |
| 2012/0140166 A1 | 6/2012 | Zhao |
| 2012/0238904 A1 | 9/2012 | Manns et al. |
| 2012/0249955 A1 | 10/2012 | Sarver et al. |
| 2012/0310337 A1 | 12/2012 | Hacker et al. |
| 2013/0050637 A1 | 2/2013 | Roffman et al. |
| 2013/0226294 A1 | 8/2013 | Van Der Mooren et al. |
| 2013/0307965 A1 | 11/2013 | Widman et al. |
| 2013/0314669 A1 | 11/2013 | Levin et al. |
| 2013/0345807 A1 | 12/2013 | Olsen et al. |
| 2014/0016088 A1 | 1/2014 | De Rossi et al. |
| 2014/0135919 A1 | 5/2014 | Gontijo et al. |
| 2014/0160436 A1 | 6/2014 | Kasthurirangan et al. |
| 2014/0176904 A1 | 6/2014 | Lai |
| 2014/0268042 A1 | 9/2014 | Bor et al. |
| 2014/0293426 A1 | 10/2014 | Dobschal |
| 2014/0320805 A1 | 10/2014 | Wilzbach et al. |
| 2015/0062529 A1 | 3/2015 | Kasthurirangan et al. |
| 2015/0138350 A1 | 5/2015 | Videcoq |
| 2015/0250583 A1 | 9/2015 | Rosen et al. |
| 2015/0320547 A1 | 11/2015 | Rosen et al. |
| 2015/0359625 A1 | 12/2015 | Argal et al. |
| 2015/0362746 A1 | 12/2015 | Skudder et al. |
| 2015/0379348 A1 | 12/2015 | Whritenor et al. |
| 2016/0157997 A1 | 6/2016 | Gerlach et al. |
| 2016/0161364 A1* | 6/2016 | Alarcon Heredia ............ G01M 11/0292 356/124.5 |
| 2016/0299355 A1 | 10/2016 | Biemold et al. |
| 2016/0335474 A1 | 11/2016 | Santos-Villalobos et al. |
| 2017/0189233 A1 | 7/2017 | Dewey et al. |

FOREIGN PATENT DOCUMENTS

| | | |
|---|---|---|
| DE | 102005022683 A1 | 11/2006 |
| EP | 226400 A2 | 6/1987 |
| EP | 227357 A2 | 7/1987 |
| EP | 3343067 A1 | 11/1989 |
| EP | D457553 A2 | 11/1991 |
| EP | 681198 A1 | 11/1995 |
| EP | 0538126 B1 | 9/1996 |
| EP | D810427 A1 | 12/1997 |
| EP | 3926531 A1 | 6/1999 |
| EP | 949529 A2 | 10/1999 |
| EP | 957331 A2 | 11/1999 |
| EP | 1424049 A1 | 6/2004 |
| EP | 1857077 A1 | 11/2007 |
| EP | 1310267 B1 | 1/2008 |
| EP | 1424049 B1 | 6/2009 |
| EP | 2631891 A1 | 8/2013 |
| EP | 2653095 A1 | 10/2013 |
| EP | 3059575 A1 | 8/2016 |
| FR | 2745711 A1 | 9/1997 |
| GB | 2433782 A | 7/2007 |
| GB | 2488802 A | 9/2012 |
| JP | 2010200915 A | 9/2010 |
| WO | 8603961 A1 | 7/1986 |
| WO | 9222264 A1 | 12/1992 |
| WO | 9303409 A1 | 2/1993 |
| WO | 9507487 A1 | 3/1995 |
| WO | 9856315 A1 | 12/1998 |
| WO | 9905499 A1 | 2/1999 |
| WO | 0019906 A1 | 4/2000 |
| WO | 0111418 A1 | 2/2001 |
| WO | 0135868 A1 | 5/2001 |
| WO | 0154569 A1 | 8/2001 |
| WO | 0163344 A1 | 8/2001 |
| WO | 0182839 A1 | 11/2001 |
| WO | 0185016 A2 | 11/2001 |
| WO | 0189424 A1 | 11/2001 |
| WO | 0221194 A2 | 3/2002 |
| WO | 02074210 A2 | 9/2002 |
| WO | 03009053 A1 | 1/2003 |
| WO | 04028356 A1 | 4/2004 |
| WO | 2004034129 A1 | 4/2004 |
| WO | 2004053568 A1 | 6/2004 |
| WO | 2004079637 A1 | 9/2004 |
| WO | 2004090611 A2 | 10/2004 |
| WO | 2004096014 A2 | 11/2004 |
| WO | 05019906 A1 | 3/2005 |
| WO | 2005079546 A2 | 9/2005 |
| WO | 06025726 A1 | 3/2006 |
| WO | 2006032263 A2 | 3/2006 |
| WO | 2006047698 A1 | 5/2006 |
| WO | 06060477 A2 | 6/2006 |
| WO | 2006060480 A2 | 6/2006 |
| WO | 2007067872 A2 | 6/2007 |
| WO | 2007092948 A1 | 8/2007 |
| WO | 2007133384 A2 | 11/2007 |
| WO | 2007142981 A2 | 12/2007 |
| WO | 2008045847 A2 | 4/2008 |
| WO | 2008083283 A2 | 7/2008 |
| WO | 2009020963 A1 | 2/2009 |
| WO | 2009029515 A1 | 3/2009 |
| WO | 2009076670 A1 | 6/2009 |
| WO | 2009105567 A1 | 8/2009 |
| WO | 2009137491 A1 | 11/2009 |
| WO | 2010009254 A1 | 1/2010 |
| WO | 2010009257 A1 | 1/2010 |
| WO | 2010028654 A1 | 3/2010 |
| WO | 2012052585 A1 | 4/2012 |
| WO | 2012074742 A1 | 6/2012 |
| WO | 2012083143 A1 | 6/2012 |
| WO | 2012085917 A1 | 6/2012 |
| WO | 2012154597 A1 | 11/2012 |
| WO | 2012166797 A1 | 12/2012 |
| WO | 2015022215 A1 | 2/2015 |
| WO | 2016032397 A1 | 3/2016 |
| WO | 2016087914 A1 | 6/2016 |
| WO | 2016123167 A1 | 8/2016 |

OTHER PUBLICATIONS

Morlock, R., et al., "Patient-Reported Spectacle Independence Questionnaire (PRSIQ): Development and Validation," American Journal of Ophthalmology, Jun. 2017, vol. 178, pp. 101-114.

Rosen R.,et al., "A Bayesian Method Using through Focus Visual Acuity to Predict Rates of Spectacle Wear for Pseudophakic patients," Investigative Ophthalmology & Visual Science, Jul. 2018, vol. 59 (9), pp. 1075, ARVO Annual Meeting Abstract, Retrieved from the Internet: (URL: https://iovs.arvojournals.org/article.aspx?articleid=2693341&resultClick=1).

Abelman H., et al. "Tolerance and Nature of Residual Refraction in Symmetric Power Space as Principal Lens Powers and Meridians Change," Computational and Mathematical Methods in Medicine, Article ID 492383, 2014, vol. 2014, pp. 1-12,.

Alfonso J.F., et al., "Prospective Study of the Acri.LISA Bifocal Intraocular Lens," Journal of Cataract Refractive Surgery, Nov. 2007, vol. 33 (11), pp. 1930-1935.

(56) References Cited

OTHER PUBLICATIONS

Alio J.L., et al., "Phakic Anterior Chamber Lenses for the Correction of Myopia: A 7-Year Cumulative Analysis of Complications in 263 Cases," Ophthalmology, Mar. 1999, vol. 106 (3), pp. 458-466.
Apple D.J., et al., "Anterior Chamber Lenses Part 1: Complications and Pathology and a Review of Designs," Journal of Cataract Refractive Surgery, Mar. 1987, vol. 13 (2), pp. 157-174.
Apple D.J., et al., Eds., "Intraocular Lenses: Evolution, Designs, Complications and Pathology," in: New Concepts in Intraocular Lens Implantation, Williams & Wilkins publisher, Jan. 1989, vol. 22 (36), pp. 205-221.
Apple D.J., et al., Eds., "Intraocular Lenses: Evolution, Designs, Complications and Pathology," in: New Concepts in Intraocular Lens Implantation, Williams & Wilkins publisher, Jan. 1989, vol. 36 (1), pp. 21-36.
Baikoff G., et al., "Angle-fixated Anterior Chamber Phakic Intraocular Lens for Myopia 7 to -19 Diopters," Journal of Refractive Surgery, May-Jun. 1998, vol. 14 (3), pp. 282-292.
Baumeister M., et al., "Tilt and Decentration of Spherical and Aspheric Intraocular Lenses: Effect on Higher-Order Aberrations," Journal of Cataract & Refractive Surgery, 2009, vol. 35 (6), pp. 1006-1012.
Brainard D.H., The Psychophysics Toolbox, Spatial Vision, vol. 10, pp. 433-436.
Brown W.L., "Revisions to Tolerances in Cylinder Axis and in Progressive Addition Lens Power in ANSI Z80.1-2005," Optometry, 2006, vol. 77 (7), pp. 343-349.
Canovas C., et al., "Customized Eye Models for Determining Optimized Intraocular Lenses Power," Biomedical Optics Express, Jun. 1, 2011, vol. 2 (6), pp. 1649-1662.
Canovas C., et al., "Hybrid Adaptive-Optics Visual Simulator," Optical Letters, Jan. 15, 2010, vol. 35 (2), pp. 196-198.
Cheng X., et al., "Predicting Subjective Judgment of Best Focus with Objective Image Quality Metrics," Journal of Vision, Apr. 2004, vol. 4 (4), pp. 310-321.
CILCO Advertisement Brochure, Oct. 1982, 3 pages.
Cohen A.L., "Practical Design of a Bifocal Hologram Contact Lens or Intraocular Lens," Applied Optics, Jul. 1, 1992, vol. 31 (19), pp. 3750-3754.
De Almeida M.S., et al., "Different Schematic Eyes and their Accuracy to the in Vivo Eye: A Quantitative Comparison Study," Brazilian Journal of Physics, Jun. 2007, vol. 37 (2A), 10 pages.
Diffractive Lenses for Extended Depth of Focus and Presbyopic Correction, Presentation from Wavefront Congress held on Feb. 15, 2008, Rochester, New York.
Doskolovich L.L., et al., "Special Diffractive Lenses," Lens and Optical Systems Design, Apr. 1992, vol. 1780, pp. 393-402.
Einighammer H.J., "The Individual Virtual Eye", Dissertation, 2008, 157 pages.
Gobbi P.G., et al., "Far and Near Visual Acuity with Multifocal Intraocular Lenses in an Optomechanical Eye Model with Imaging Capability," Journal of Cataract and Refractive Surgery, 2007, vol. 33 (6), pp. 1082-1094.
Gobbi P.G., et al., "Optomechanical Eye Model with Imaging Capabilities for Objective Evaluation of Intraocular Lenses," Journal of Cataract and Refractive Surgery, 2006, vol. 32 (4), pp. 643-651.
Hill W., et al., "Monte Carlo Simulation of Expected Outcomes with the Acrysof Toric Intraocular Lens," BMC Ophthalmology, Oct. 2008, vol. 8, pp. 22.
Kim J.H., et al., "The Analysis of Predicted Capsular Bag Diameter using Modified Model of Capsule Measuring Ring in Asians," Clinical and Experimental Ophthalmology, Apr. 2008, vol. 36 (3), pp. 238-244.
Kim M.J., et al., "Objective Evaluation of Through-Focus Optical Performance of Presbyopia-Correcting Intraocular Lenses Using an Optical Bench System," Journal of Cataract and Refractive Surgery, 2011, vol. 37 (7), pp. 1305-1312.
Klein S.A., "Optimal Corneal Ablation for Eyes with Arbitrary Hartmann-Shack Aberrations," Journal of the Optical Society of America A, 1998, vol. 15 (9), pp. 2580-2588.
Liang J., et al, "Objective Measurement Of Wave Aberrations Of The Human Eye With The Use Of A Hartmann-Shack Wave-Front Sensor," Journal of the Optical Society of America, 1994, vol. 11 (7), pp. 1949-1957.
Liou H.L., et al., "Anatomically Accurate, Finite Model Eye for Optical Modeling," Journal of Optical Society of America, Aug. 1997, vol. 14 (8), pp. 1684-1695.
Liou H.L., et al., "The Prediction of Spherical Aberration with Schematic Eyes," Ophthalmic and Physiological Optics, Jan. 1996, vol. 16 (4), pp. 348-354.
Marinho A., "Results are Encouraging for Phakic IOLs, but More Work is needed," Refractive Surgery, Feb. 2000, p. 12, 15.
Marsack J.D., et al., "Metrics of Optical Quality Derived from Wave Aberrations Predict Visual Performance," Journal of Vision, Apr. 2004, vol. 4 (4), pp. 322-328.
Menapace R., "The Capsular Tension Rings," Journal of Cataract & Refractive Surgery, Dec. 10, 2008, Chap. 3, pp. 27-44.
Mencucci R., et al., "Clinical outcomes and rotational stability of a 4-haptic toric intraocular lens in myopic eyes," Journal of Cataract & Refractive Surgery, Sep. 2014, vol. 40 (9), pp. 1479-1487.
Monsoriu J.A., et al., "Devil's Lenses," Optics Express, Oct. 17, 2007, vol. 15 (21), pp. 13858-13864.
Navarro R., et al., "Accommodation-Dependent Model of the Human Eye with Aspherics," Journal of the Optical Society of America, Aug. 1985, vol. 2 (8), pp. 1273-1281.
Nio Y.K., et al., "Effect of Intraocular Lens Implantation on Visual Acuity, Contrast Sensitivity, and Depth of Focus," Journal of Cataract and Refractive Surgery, Nov. 2003, vol. 29 (11), pp. 2073-2081.
Norrby S., et al., "Model Eyes for Evaluation of Intraocular Lenses," Applied Optics, Sep. 7, 2007, vol. 46 (26), pp. 6595-6605.
Olsen T., "Simple Method to Calculate the Surgically Induced Refractive Change," Journal of Cataract & Refractive Surgery, Mar. 1993, vol. 19 (2), pp. 319-320.
Peli E., et al., "Appearance of Images Through A Multifocal Intraocular Lens," Journal of the Optical Society of America, 2001, vol. 18 (2), pp. 302-309.
Piers P.A., et al., "Eye Models for the Prediction of Contrast Vision in Patients with New Intraocular Lens Designs," Optics Letters, Apr. 1, 2004, vol. 29 (7), pp. 733-735.
Piers P.A., et al., "Theoretical Comparison of Aberration-Correcting Customized and Aspheric Intraocular Lenses," Journal of Refractive Surgery, Apr. 2007, vol. 23 (4), pp. 374-384.
Praeger D.L., "Praeger Technique for the Insertion of the Copeland Radial IOL Posterior Chamber Placement," Copeland Lens, 1982, 7 pages.
Siedlecki D., et al., "Radial Gradient index Intraocular Lens: a Theoretical Model," Journal of Modern Optics, Feb. 20-Mar. 10, 2008, vol. 55 (4-5), pp. 639-647.
Strenn K., et al., "Capsular bag Shrinkage after Implantation of an Open-Loop Silicone Lens and a Poly(methyl methacrylate) Capsule Tension Ring," Journal of Cataract and Refractive Surgery, Dec. 1997, vol. 23 (10), pp. 1543-1547.
Tehrani M., et al., "Capsule Measuring Ring to Predict Capsular Bag Diameter and Follow its Course after Foldable Intraocular Lens Implantation," Journal of Cataract Refractive Surgery, Nov. 2003, vol. 29 (11), pp. 2127-2134.
Terwee T., et al., "Visualization of the Retinal Image in an Eye Model With Spherical and Aspheric, Diffractive, and Refractive Multifocal Intraocular Lenses," Journal of Refractive Surgery, Mar. 2008, vol. 24 (3), pp. 223-232.
Van Den Berg T.J., "Analysis of Intraocular Straylight, Especially in Relation to Age," Optometry and Vision Science, Feb. 1995, vol. 72 (2), pp. 52-59.
Van Meeteren A., "Calculations on the Optical Modulation Transfer Function of the Human Eye for White Light," Optica Acta, May 1974, vol. 21 (5), pp. 395-412.
Vass C., et al., "Prediction of Pseudophakic Capsular bag Diameter based on Biometric Variables," Journal of Cataract and Refractive Surgery, Oct. 1999, vol. 25 (10), pp. 1376-1381.

(56) References Cited

OTHER PUBLICATIONS

Villegas E.A., et al., "Correlation between Optical and Psychophy, Sical Parameters as a Function of Defocus," Optometry and Vision Science, Jan. 1, 2002, vol. 79 (1), pp. 60-67.

Abrahamsson M., et al., "Impairment of Contrast Sensitivity Function (CSF) as a Measure of Disability Glare," Investigative Ophthalmology & Visual Science, Jul. 1986, vol. 27 (7), pp. 1131-1136.

Aslam, T.M., et al., "Development of a Forced Choice Photographic Questionnaire For Photic Phenomena and Its Testing—Repeatability, Reliability and Validity," Ophthalmologica, Nov.-Dec. 2004, vol. 218 (6), pp. 402-410.

Beer J.M., et al., "Lasers' Spectral and Temporal Profile Can Affect Visual Glare Disability," Aviation, Space, and Environmental Medicine, Dec. 2012, vol. 83 (12), pp. 1135-1144.

Calatayud A., et al., "Imaging Quality of Multifocal Intraocular Lenses: Automated Assessment Setup," Ophthalmic and Physiological Optics, Jul. 2013, vol. 33 (4), pp. 420-426.

Fernandez E.J., et al., "Adaptive Optics Visual Simulator," Journal of Refractive Surgery, 2002, vol. 18 (5), pp. S634-S638.

Guirao A., et al., "Corneal Wave Aberration from Videokeratography: Accuracy And Limitations of the Procedure," Journal of the Optical Society of America, 2000, vol. 17 (6), pp. 955-965.

Jaeken B., et al., "Peripheral Aberrations in the Human Eye for Different Wavelengths: Off-Axis Chromatic Aberration," Journal of the Optical Society of America A, Sep. 2011, vol. 28 (9), pp. 1871-1879.

Javitt J.C., et al., "Validity and Reliability of the Cataract TyPE Spec: an Instrument For Measuring Outcomes of Cataract Extraction," American Journal of Ophthalmology, Aug. 2003, vol. 136 (2), pp. 285-290.

Jendritza B.B., et al., "Wavefront-Guided Excimer Laser Vision Correction after Multifocal IOL Implantation," Journal of Refractive Surgery, Mar. 2008, vol. 24 (3), pp. 274-279.

Johnson C.A., "Psychophysical Factors that Have Been Applied to Clinical Perimetry," Vision Research, Sep. 2013, vol. 90, pp. 25-31.

Lesmes L.A., et al., "Bayesian Adaptive Estimation of the Contrast Sensitivity Function: the Quick CSF Method," Journal of Vision, Mar. 2010, vol. 10 (3) 17, pp. 1-21.

Ortiz, C., et al., "Quantification and Monitoring of Visual Disturbances for patients with cataracts using Halo v1.0 software," Department of Optics, Laboratory of Vision Sciences and Applications, University of Granada, IWBBIO 2013, Mar. 20, 2013, XP055596332, Proceedings, 8 Pages.

Vitale S., et al., "The Refractive Status and Vision Profile: A Questionnaire to Measure Vision-Related Quality of Life in Persons with Refractive Error," Ophthalmology, Aug. 2000, vol. 107 (8), pp. 1529-1539.

Weeber H.A., et al., "Influence of Corneal Aberrations on Dysphotopsia with Multifocal IOLs," Arvo, 2011, Abstract.

Weeber H.A., et al., "Influence of Corneal Aberrations on Dysphotopsia with Multifocal IOLs," RD3115, 2011.

Weeber H.A., et al., "Optical and Visual Performance of Patient Populations Implanted with Monofocal and Multifocal IOLs in the Presence of Defocus," Investigative Ophthalmology & Visual Science, 2010, vol. 51, E-Abstract 5751.

Weeber H.A., et al., "Population-based Visual Acuity in the Presence of Defocus Well Predicted By Classical Theory," Journal of Biomedical Optics, 2010, vol. 15 (4), pp. 040509.

Weeber H.A., et al., "Theoretical Performance of Intraocular Lenses Correcting Both Spherical and Chromatic Aberration," Journal of Refractive Surgery, 2012, vol. 28 (1), pp. 48-52.

\* cited by examiner

● = spectacle wear ● = spectacle independent ◐ = near VA better than 0.1 ⊕ = near VA worse than 0.1

P(SI): ● ● ● ● ⊕ vs ● ● ● ● ● ● ● ● ● ● ● ● ● ● ● ● ● ● ● ●  = 5/20 = 25%

P(VA>0.1|SI): ● ● ● vs ● ●  = 3/5 = 60%

P(VA>0.1): ● ● ● vs ● ● ● ● ● ● ● ● ● ● ● ● ● ● ● ⊕ ⊕  = 4/20 = 20%

P(SI|VA>0.1): ● ● ● vs ●  = 3/4 = 75%

$$P(SI|VA>0.1) = \frac{P(VA>0.1|SI)P(SI)}{P(VA>0.1)} = \frac{0.6 * 0.25}{0.20} = 75\%$$

FIG. 2

INTRAOCULAR LENSES THAT IMPROVE POST-SURGICAL SPECTACLE INDEPENDENT AND METHODS OF MANUFACTURING THEREOF

CROSS REFERENCES TO RELATED APPLICATIONS

This application claims the benefit under 35 U.S.C. § 119(e) of U.S. Provisional Patent Application No. 62/593,162, filed Nov. 30, 2017, which is incorporated herein by reference in its entirety.

BACKGROUND OF THE INVENTION

Field of the Invention

This application is related to systems and methods of selecting, designing and manufacturing intraocular lenses that improve post-surgical spectacle independence in cataract patients.

Description of the Related Art

Retinal image quality of intraocular lenses when implanted in the eye of a patient can be estimated from different metrics obtained from pre-clinical measurements. For example, through focus visual acuity for psuedophakic patients can be predicted from metrics based on various pre-clinical measurements. However, many of the metrics used to predict post-surgical optical performance of intraocular lenses are unable to reliably predict spectacle independence for psuedophakic patients. Spectacle independence is a desired outcome following cataract surgery for most patients. Accordingly, it would be desirable to develop new techniques to reliably predict the spectacle independence for pseudophakic patients receiving different IOLs.

SUMMARY OF THE INVENTION

This application contemplates systems and methods of predicting spectacle independence utilizing pre-clinical data to simulate and predict the expected percentage of patients that will be spectacle independent following cataract surgery with an IOL in which pre-clinical (measured or simulated) data is available. One piece of pre-clinical data that can be used to predict spectacle independence is through-focus visual acuity at one or more defocus positions. For example, it may be possible to predict spectacle independence based on through-focus visual acuity at near distances, such as, for example, near distances greater than or equal to about 25 cm and less than or equal to about 50 cm. However, there is limited information on whether a high peak in through-focus visual acuity at one near distance (e.g., 40 cm) is a better predictor of spectacle independence or whether a flat but lower through-focus visual acuity at a plurality of near distance values between about 25 cm and about 50 cm is a better predictor of spectacle independence. The methods and systems contemplated in this application are based on applying Bayesian models to an initial data set including known spectacle independence information obtained from clinical studies gathering responses to questions in a questionnaire from different patients implanted with different intraocular lenses for which measured or simulated pre-clinical data is available and calculating the probability that a patient would be spectacle independent for a certain value of visual acuity at a certain defocus distance. Since the initial data set is based on a small number of patients (e.g., less than or equal to about 500, less than or equal to about 1000, or less than or equal to about 2000), the prediction of spectacle independence from through-focus visual acuity values at one or more defocus positions can be calculated using "medium data" solutions that operate on medium sized databases. Additionally, machine learning can be employed to appropriately weight and scale the contribution of through-focus visual acuity performance at various defocus distances to spectacle independence.

One innovative aspect of the subject matter disclosed herein is implemented in an optical system configured to select an intraocular lens (IOL) from a plurality of IOLs for manufacture or for implantation into a patient eye, the selected IOL configured or to be manufactured to improve post-surgical spectacle independence outcome for the patient. The optical system comprises a processor configured to execute programmable instructions stored in a non-transitory computer storage medium; and a population database comprising clinical data for a plurality of patients less than or equal to about 5000 implanted with one of the plurality of IOLs, the clinical data comprising information related to spectacle independence for a plurality of values of visual acuity between about −0.2 log MAR and about 1 log MAR at various defocus conditions between about −5 D and 0 D, wherein the information related to spectacle independence is based on responses of the patients implanted with one of the plurality of IOLs to a questionnaire. The processor is configured to calculate for each of the plurality of IOLs, a probability of being spectacle independent for visual acuity equal to a threshold value between about −0.2 log MAR and about 1 log MAR at at least one defocus conditions between about −5 D and 0 D based on the information related to spectacle independence obtained from the population database; and identify one of the plurality of IOLs having a higher probability of being spectacle independent for manufacture or for implantation into the patient's eye.

The processor can be further configured to calculate for each of the plurality of IOLs, a probability of being spectacle independent for visual acuity equal to a threshold value between about −0.2 log MAR and about 1 log MAR at at least two or more defocus conditions between about −5 D and 0 D. The processor can be further configured to assign a weight to the probability of being spectacle independent for visual acuity equal to a threshold value between about −0.2 log MAR and about 1 log MAR at at least two or more defocus conditions between about −5 D and 0 D. The processor can be configured to execute a machine learning algorithm to determine the weight.

Another innovative aspect of the subject matter disclosed herein can be embodied in an optical system configured to identify an intraocular lens (IOL) that will improve post-surgical spectacle independence. The system comprises a processor configured to execute programmable instructions stored in a non-transitory computer storage medium to calculate a probability of achieving spectacle independence for at least two IOLs based on clinical data providing visual acuity at a first defocus position for the at least two IOLs in a population of patients implanted with one of the at least two IOLs; and identify one of the at least two IOLs having higher probability of achieving spectacle independence.

The processor can be further configured to calculate the probability of achieving spectacle independence for at least two IOLs based on at least one of: clinical data providing visual acuity at a second defocus position for the at least two IOLs in the population; standard deviation of pre-clinical visual acuity for the at least two IOLs at the first or the second defocus positions; clinical data providing minimum readable print size in mm in the population; modulation transfer function (MTF) at one or more frequencies at different distances for different pupil sizes; or area under the modulation transfer function at one or more frequencies at different distances for different pupil sizes.

The first defocus position can be about −2.5 D corresponding to a distance of about 40 cm. The second defocus position can have a value between about −5 D and about −0.5 D. A size of the population can be less than about 1000. The processor can be configured to execute programmable instructions stored in a non-transitory computer storage medium to transmit one or more parameters of the identified IOL to a display device or an IOL manufacturing system.

Yet another innovative aspect of the subject matter disclosed herein is implemented in a system for predicting post-surgical spectacle independence of one or more IOLs, the system comprising a processor configured to execute programmable instructions stored in a non-transitory computer storage medium to calculate a probability of achieving spectacle independence for the one or more IOLs based on clinical data providing visual acuity at one or more defocus position for the one or more IOLs in a population of patients implanted with one of the one or more IOLs.

The processor can be further configured to execute programmable instructions stored in a non-transitory computer storage medium to calculate the probability of achieving spectacle independent based on one or more combinations of visual acuity at at least two or more defocus positions for the one or more IOLs in the population. The processor can be further configured to execute programmable instructions stored in a non-transitory computer storage medium to assign weights to the one or more combinations of visual acuity. The weights can be determined based on a machine learning algorithm.

An innovative aspect of the subject matter disclosed herein is implemented in a method of manufacturing an IOL comprising: receiving one or more parameters of an IOL selected from a plurality of IOLs based on calculating a probability of achieving spectacle independence for the plurality of IOLs from clinical data providing visual acuity at one or more defocus position for the plurality of IOLs in a population of patients implanted with one of the plurality of IOLs; and manufacturing the selected IOL.

BRIEF DESCRIPTION OF THE DRAWINGS

Embodiments of the present invention may be better understood from the following detailed description when read in conjunction with the accompanying drawings. Such embodiments, which are for illustrative purposes only, depict novel and non-obvious aspects of the invention. The drawings include the following figures:

FIG. 2 shows an example method of calculating probability of an event using Bayesian statistics.

DETAILED DESCRIPTION OF THE PREFERRED EMBODIMENT

Each and every feature described herein, and each and every combination of two or more of such features, is included within the scope of the present invention provided that the features included in such a combination are not mutually inconsistent.

As used herein, the terms "about" or "approximately", when used in reference to a Diopter value of an optical power, mean within plus or minus 0.25 Diopter of the referenced optical power(s). As used herein, the terms "about" or "approximately", when used in reference to a percentage (%), mean within plus or minus one percent (±1%). As used herein, the terms "about" or "approximately", when used in reference to a linear dimension (e.g., length, width, thickness, distance, etc.) mean within plus or minus one percent (1%) of the value of the referenced linear dimension.

Spectacle independence is a highly desired outcome following cataract surgery. It is possible to predict through-focus visual acuity (VA) for different implementations of intraocular lenses (IOLs) based on pre-clinical data using mathematical models. Through-focus VA can be predicted for one or more defocus values based on available pre-clinical data for an IOL including but not limited to IOL characteristics such as refractive index of the IOL, radii of curvature, diffraction power, diffraction step height, transition zones and IOL thickness. These characteristics can be used in a ray tracing simulation software to predict through-focus MTF, which can predict through-focus VA. IOL designs can be optimized to achieve a desired optical performance based on the predicted values of through-focus VA.

The predicted through-focus VA at one or more defocus values can be based on an output generated by an electronic processor from available pre-clinical data of the IOL input to the electronic processor. The electronic processor can be configured to execute instructions stored on a non-transitory hardware storage medium to generate the output. An example electronic processing system is discussed in detail below with reference to FIG. 6. The through-focus VA at one or more defocus values for an IOL can be measured using a Log MAR chart that can comprise rows of letters. The through-focus VA of an implementation of an IOL is 0 Log MAR if the implementation of the IOL can resolve details as small as 1 minute of visual angle. A series of negative powered lenses can be placed in front of the IOL to simulate near distance vision. In this manner through-focus VA at a plurality of defocus values can be measured to obtain a defocus curve. Without any loss of generality, a defocus value of −2.5 Diopters can correspond to a near distance value of about 40 cm. Defocus values less than −2.5 Diopters correspond to near distance values less than about 40 cm.

Figure 1:
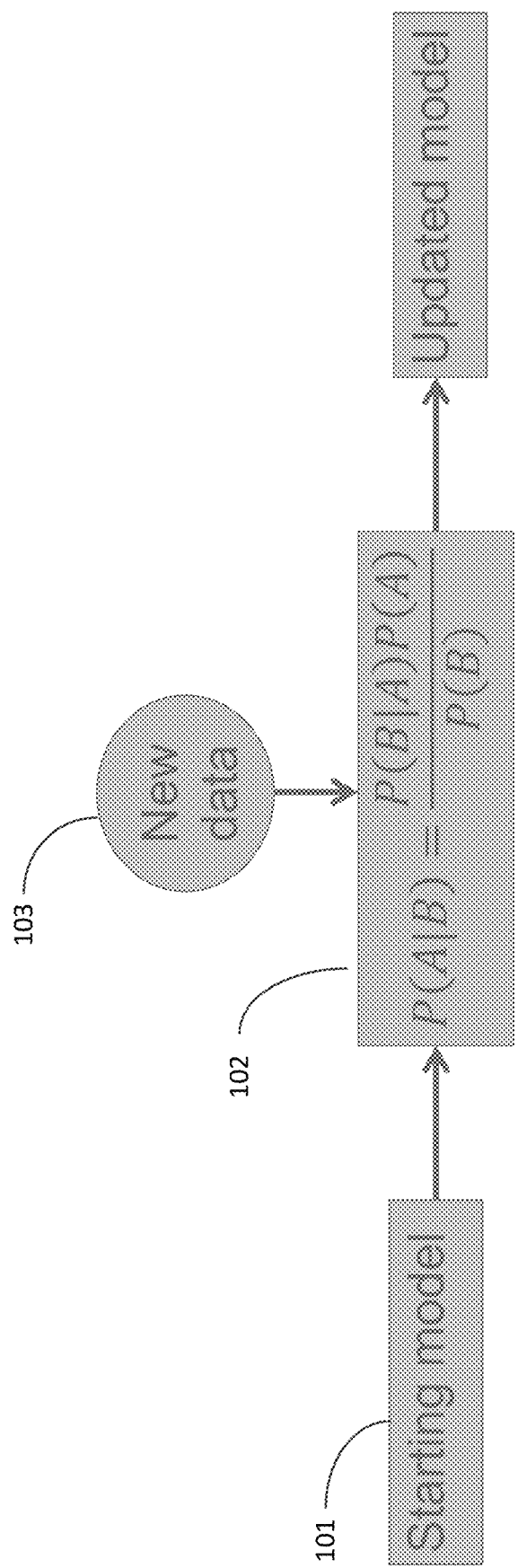
FIG. 1 is a flowchart illustrating a method of predicting values using Bayesian analysis.

This application contemplates systems and methods to predict the expected percentage of patients that will be spectacle independent based when implanted with an IOL whose pre-clinical data is available. The spectacle independence can be estimated using Bayesian analysis. Bayesian analysis is a statistical procedure which combines prior distribution of one or more population parameters before any data is observed with observed information in a sample to obtain an updated probability distribution for the one or more parameters. FIG. 1 illustrates an implementation of the Bayesian analysis. As shown in FIG. 1, the Bayesian analysis begins with a starting model 101. The starting model can be a prior probability density function (pdf) of different hypotheses associated with certain probabilities of being true. New data is collected from a sample of the population as shown in block 103. The new data can be conditional on the different hypotheses. The pdf of the different hypotheses is updated based on the prior pdf and the new data using Bayes' rule shown in block 102. Mathematical Bayes' rule is given by the equation $$P(A \mid B) = \frac{P(B \mid A) * P(A)}{P(B)}$$

When using Bayes analysis to estimate spectacle independence from pre-clinical data, A can correspond to the pdf of different percentages of spectacle independence, and B can correspond to the clinical data that is used to predict spectacle independence.

The clinical data can be a singular value or a multidimensional value. Through-focus VA is an example of a multidimensional value (for example, VA at −3 D, at −2.5 D, at −2 D, . . . , at 0 D of defocus). A singular value can also be used to predict the percentage of spectacle independence. Predicting spectacle independence based on a singular value can be simple and computationally less intensive. Singular values used for predicting spectacle independence can include (i) VA at near distance (e.g., 40 cm), (ii) VA at any other distance, (iii) standard deviation of VA in a certain distance/defocus range which can be a measure of the variability/consistency of VA in the distance/defocus range, (iv) minimum readable print size in mm calculated by predicted angular VA which is converted to stroke width of letters in mm at that distance and taking the minimum value. This corresponds to best distance at which a patient can view small print, (v) modulation transfer function (MTF) at certain spatial frequencies at certain distances and pupil sizes, or (vi) Area under MTF curve at certain distances and pupil sizes.

For singular value metrics B, A can comprise a plurality of probabilities i of spectacle independence, such as 1%, 2%, 3%, . . . , 99%, 100%. The conditional probability of $P(A\_i|B)$ can be calculated using Bayes' rule by the equation $$P(A\_i \mid B) = \frac{P(B \mid A\_i) * P(A\_i)}{P(B)}$$

The plurality of probabilities of different percentages of spectacle independence $P(A\_i)$ can be determined based on a prior model of spectacle independence, such as having a linear function between 5% and 95%, in the VA range from 0.6 Log MAR to 0 Log MAR at a certain defocus value (e.g., −2.5 D). Bayes analysis can then be used to estimate the probability $P(B|A\_i)$, the probability of the set given clinical data assuming spectacle independence A_i through direct calculation from the clinical data as well as the model. P(B) can be considered as a normalization factor.

The method discussed above can be applied for multidimensional values as well. However, some modification and additional techniques may be required when the multidimensional value metric is through-focus VA at different defocus values, since VA at different defocus values may be correlated. Due to the relatively large number of defocus positions, correcting for interaction effects may not possible. In some implementations of Bayesian analysis that employs through-focus VA at different defocus values as the pre-clinical metric, a multidimensional matrix including all possible combinations of VA values at different defocus values may be generated. This matrix can be sampled, for example, in steps of 0.5 D and 0.1 Log MAR. At each such combination there is a pdf for different percentages of spectacle independence. The data added into the matrix could be additive for any VA at any value higher than the given curve for, thus phrasing the probabilities as "having VA of x or higher".

This method is illustrated in FIG. 2 which has a sample of 20 subjects. Five of the 20 subjects are spectacle independent as shown in block 201 and the remaining fifteen wear spectacles as shown in block 202. Thus, the probability of spectacle independence P(SI) is equal to 5/20 or 25%. Of the five subjects who are spectacle independent, three have a visual acuity greater than 0.1 as shown in block 203 while two have a visual acuity less than 0.1 as shown in block 204. Thus, the conditional probability of having visual acuity greater than 0.1 when being spectacle independent P(VA>0.1|SI) is equal to 3/5 or 60%. Four of the 20 subjects have visual acuity greater than 0.1 as shown in block 205 while sixteen of the 20 subjects have visual acuity less than 0.1 as shown in block 206. Thus, the probability that visual acuity is greater than 0.1 P(VA>0.1) is equal to 4/20 or 20%. Three subjects having visual acuity greater than 0.1 are spectacle independent as shown in block 207 while 1 subject having visual acuity greater than 0.1 is not spectacle independent as shown in block 208. Thus, the probability of being spectacle independent given visual acuity is greater than 0.1 P(SI|VA>0.1) is equal to 3/4 or 75%. The probability of being spectacle independent given visual acuity is greater than 0.1 P(SI|VA>0.1) can also be calculated using Bayes' rule as $$P(SI \mid VA > 0.1) = \frac{P(VA > 0.1 \mid SI) * P(SI)}{P(VA > 0.1)}$$

which is equal to 75%.

Another example to illustrate the method of determining spectacle independence based on visual acuity is described below. For the sake of simplicity a singular value metric is used to estimate spectacle independence, but the same techniques can be generalized when a multidimensional value is used.

Figure 3A:
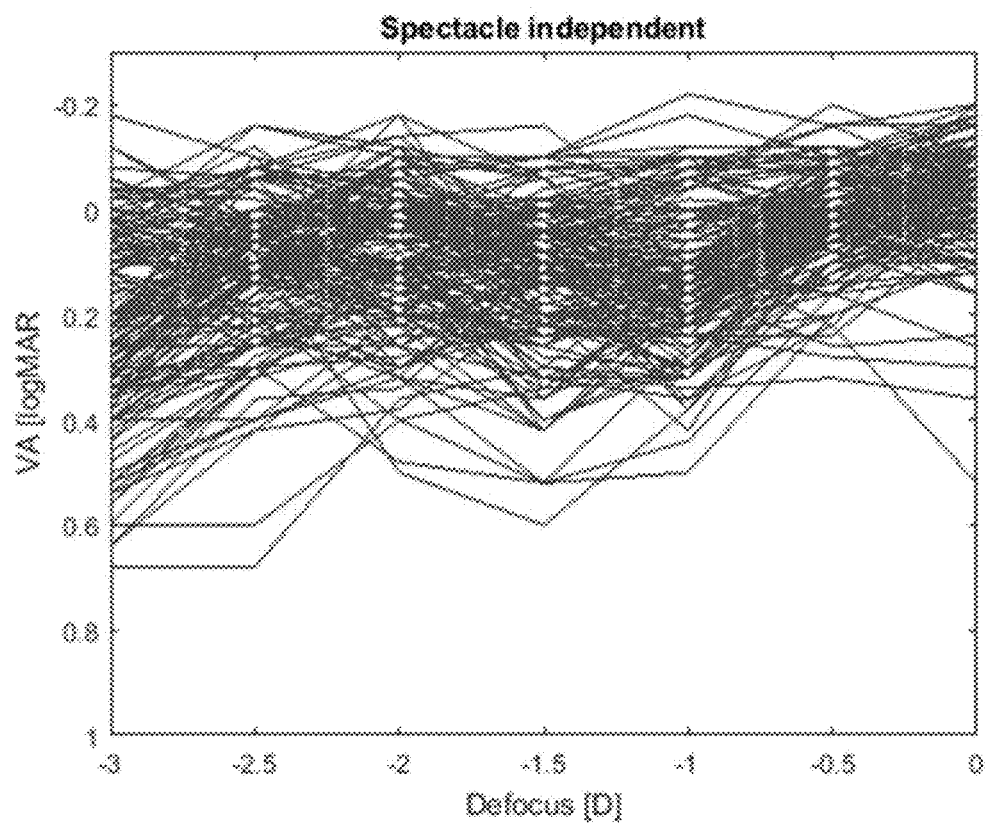
FIG. 3A is data from clinical studies for 162 pseudophakic patients that are spectacle independent.
Figure 3B:
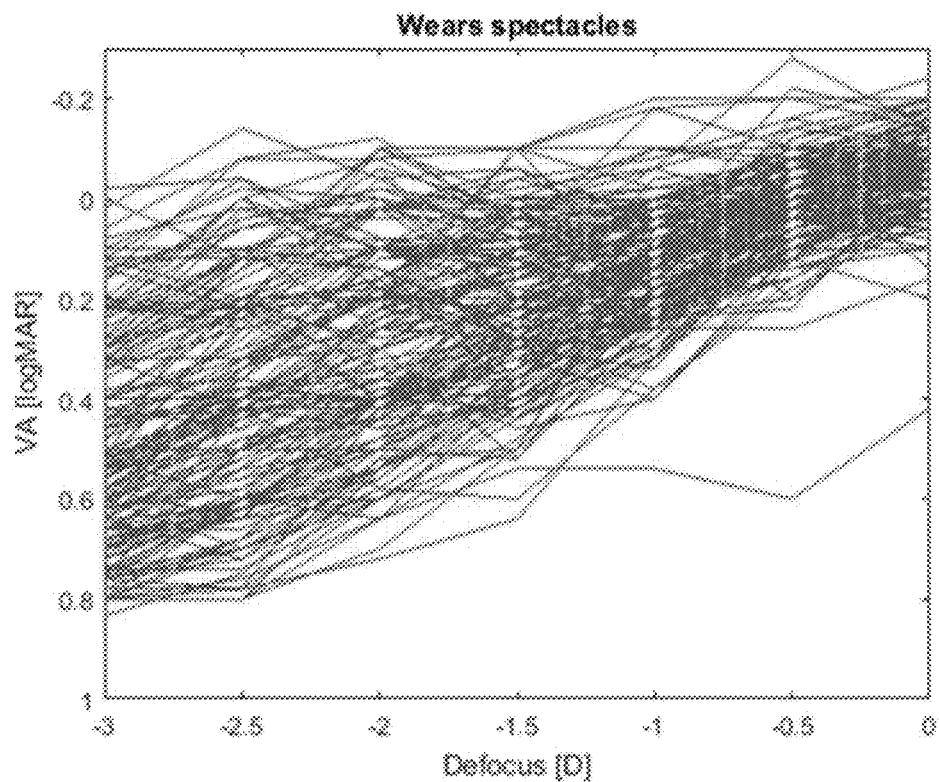
FIG. 3B is data from clinical studies for 159 pseudophakic patients that are not spectacle independent.

Consider that it is desired to investigate the probability of being spectacle independent if VA at −2.5 D is −0.05 Log MAR. From a clinical data set obtained from observation of 321 subjects, it is found that there are four subjects who are not spectacle independent and have VA at −2.5 D greater than or equal to −0.05 and there are 16 subjects who are spectacle independent and have VA at −2.5 D greater than or equal to −0.05. From the clinical data set, it is further observed that there are 155 subjects who are not spectacle independent and have VA at −2.5 D less than −0.05 and 146 subjects who are spectacle independent and have VA at −2.5 D less than −0.05. FIG. 3A shows the defocus curve for spectacle independent subjects and FIG. 3B shows the defocus curve for subjects who wear spectacles.

Based on the information, the probability of being spectacle independent when VA at −2.5 D is greater than or equal to −0.05 P(SI|VA at −2.5 D>−0.05)=P(VA at −2.5 D>−0.05|SI)*P(SI)/P(VA at −2.5 D>−0.05) which is equal to (16/162)*(162/321)/(20/321) which is equal to 80%.

Figure 4:
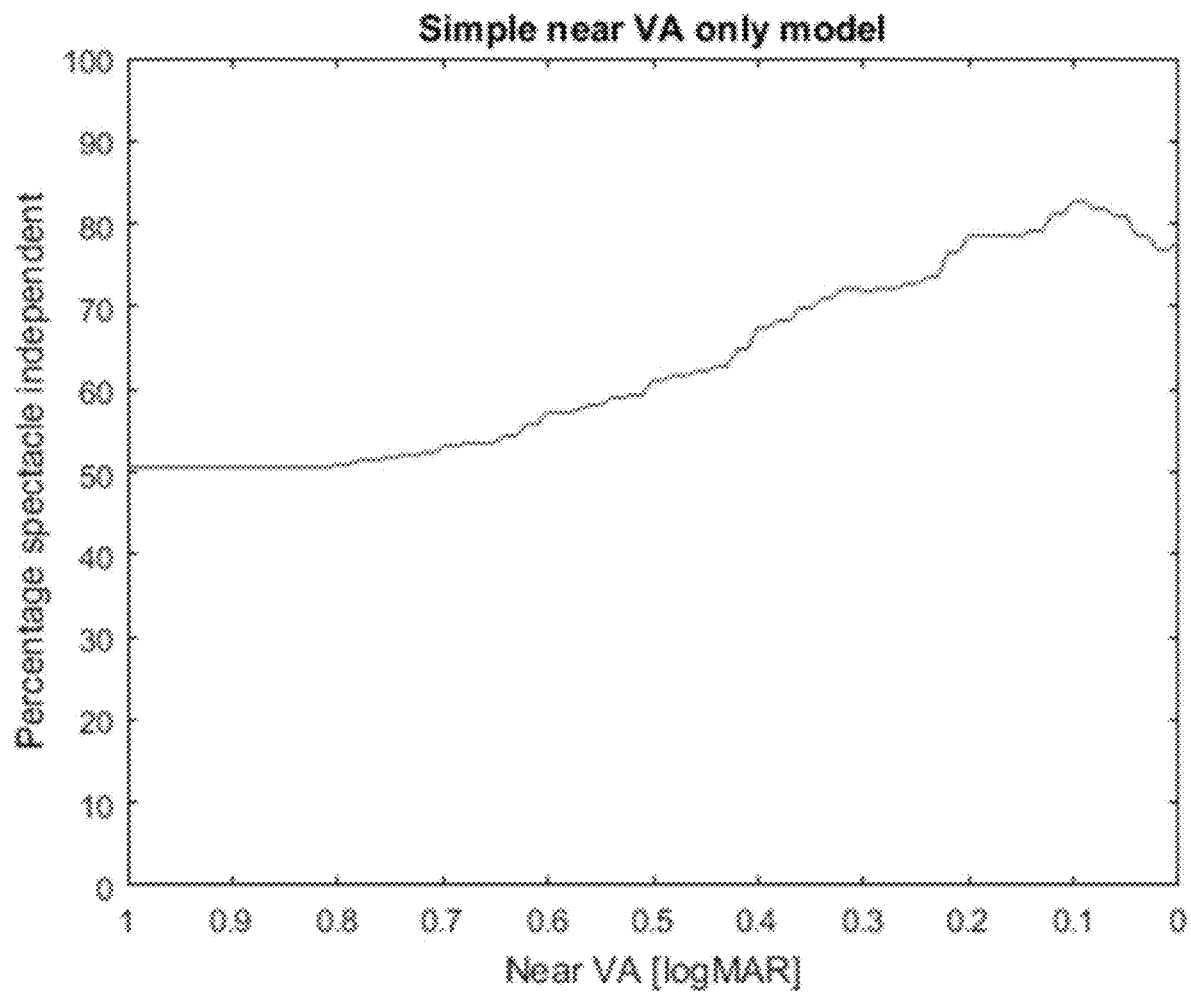
FIG. 4 is a graph showing a predicted percentage of patients who are spectacle independent obtained using a simple model based on near distance visual acuity.

FIG. 4 shows the percentage of spectacle independence for different values of near distance VA obtained using a singular value as described above. It is noted from FIG. 4 that using only near distance VA as a predictor for spectacle independence has an 80% of achieving spectacle independence, regardless of the value of near distance VA of the lens.

It is further noted from FIG. 4 that if VA at all distances is low then the probability of being spectacle independent is about 50%. However, in the clinical data set, there were 102 subjects who are not spectacle independent and have a VA of 0.3 Log MAR or worse, 56 subjects who are not spectacle independent and have VA better than 0.3 Log MAR, 13 subjects who are spectacle independent VA of 0.3 Log MAR or worse, and 144 subjects who are spectacle independent and have VA better than 0.3 Log MAR.

Using Bayes analysis, the probability of being spectacle dependent and having a VA of 0.3 Log MAR or worse P(SD|VA of 0.3 Log MAR or worse)=P(VA of 0.3 Log MAR or worse|SD)*P(SD)/P(VA of 0.3 Log MAR or worse) which is equal to (102/158)*(158/315)/(115/315)=88.7%. Thus, there is an 11.3% chance of being spectacle independent if the VA is 0.3 Log MAR or worse. Thus, the model of predicting spectacle independence based on singular VA value can be updated by combining the two estimates to better predict the chance of being spectacle independent given a certain VA value as described below.

Consider a vector t of length 100 with the probabilities of having 1%, 2%, 3% . . . , 99%, 100% spectacle independent at a certain value of VA. The vector t can be updated according to the example below.

Consider that the vector t has a length of 2 with a 0.5 probability of 80% being spectacle independent and 0.5 probability of 70% being spectacle independent. For VA values above −0.05 we have 4 subjects who wear spectacles and 16 subjects who don't wear spectacles. The probability of being spectacle independent for VA above −0.05, can be calculated using the $P(x)=(N!/(x!(N-x)!))*(fx)*(1-t)^{(N-x)}$ where N is total number, x is the number of spectacle independent and t is the probability. For the example above, N=20, x=16 and t=0.7 and 0.8. Accordingly, P(x) is equal to 0.13 for t=0.7 and 0.21 for t=0.8. If the initial prior pdf P(A) is [0.5, 0.5], and P(B) is applied as a standard normalization factor, P(A|B)=[0.5*0.13, 0.5*0.21]/(0.5*0.13+0.5*0.21)= 0.38 for t=0.7, and 0.62 for t=0.8. In this manner the vector t is updated. A similar technique can be applied for estimating spectacle independence for VA worse than a certain value, and the results combined using a range of methods. A skilled person would understand that it is advantageous to start with a reasonable prior pdf as the posterior probability distribution can skew towards the prior pdf when the number of subjects is low.

The abovementioned technique can also be applied to the multidimensional case, where a larger matrix is used and a combination of VA applicable to all defocus positions is selected. In such a case, the sampling may be limited. The sampling limitation can be overcome by using a two-step process, wherein first a coarse sampling is applied, e.g. steps of 0.1 Log MAR. Thereafter, if the VA of interest to test is e.g. 0.12, we combine the two nearby steps, with 80% weight to estimates for VA=0.1 and 20% weight to the estimate with VA=0.2.

The Bayesian analysis method can be expanded to cover more than a binary outcome of spectacle dependent/spectacle independent, and instead describe the probability of never wearing spectacles, of wearing spectacles a little bit of the time, some of the time, or all of the time.

The Bayesian analysis method can be expanded to incorporate other characteristics of the patients, such as age, gender, eye length, pupil size, ethnicity, corneal aberrations, life style or combinations thereof.

The Bayesian analysis method of estimating spectacle independence for different parameters can be incorporated in an IOL design and/or manufacturing process. The parameter space of IOL design allows variation of IOL characteristics such as radii of curvature, diffraction power, diffraction step height, transition zones and IOL thickness. These characteristics can be used in a ray tracing simulation software to predict through focus MTF, which can predict VA. Using Bayesian analysis, the probability of spectacle independence can be calculated, and the IOL characteristics optimized such that the highest possible spectacle independence is achieved, in conjunction with other simulated and desired constraints such as distance image quality. Bayesian analysis can also be used to predict how suitable certain treatment techniques, such as making the patients slightly myopic postoperatively can positively affect spectacle independence. Bayesian analysis to estimate spectacle independence can also be used to select an IOL for implantation in a patient that would increase the chance of the patient to be spectacle independent for a variety of tasks such as reading, viewing a smartphone, computer use or combinations thereof.

The spectacle independence of five different implementations of IOLs was predicted based on pre-clinical data based on the Bayesian analysis method described above. To predict spectacle independence, a data set of 321 patients from three different studies was used. The patients were bilaterally implanted with five different implementations of IOLs. Spectacle independence was coded as a binary outcome. Through focus VA was varied in steps of 0.5 D between −3 D and 0 D. A Bayesian model to estimate rate of spectacle independence was developed. The Bayesian model was configured to calculate probability of spectacle independence for VA better than a certain value as well as probability of spectacle dependence for VA worse than a certain value. The Bayesian model was further configured to calculate probability with different combinations of VA at different defocus values. For example, the Bayesian model was configured to (i) calculate probability of VA greater than or worse than a certain value for different single defocus values (e.g., 0 D, −0.5 D, −1 D, −1.5 D, −2 D, −2.5 D, −3 D), (ii) calculate probability of VA greater than or worse than a certain value for combinations of two different defocus values (e.g., −3 D and −2.5 D, −2 D and −1 D), and (iii) calculate probability of VA greater than or worse than a certain value for combinations of three or more different defocus values. For example, the model was configured to calculate probability of VA greater than or worse than a certain value for combination of seven different defocus values (e.g., 0 D, −0.5 D, −1 D, −1.5 D, −2 D, −2.5 D, and −3 D).

The model was trained to combine and weight the different probabilities in order to have outcomes closest to the reported rates of spectacle independence. For example, probability of VA greater than or worse than a certain value for combination of two or more different defocus values that are closer to each other was assigned a higher weight than probability of VA greater than or worse than a certain value for combination of two or more different defocus values that are farther from each other. As another example, probability of VA greater than or worse than a certain value for different defocus values corresponding to near distances between 25 cm and about 40 cm can be assigned a higher weight than VA at other defocus values.

The table below shows the clinically measured percentage spectacle independence for five different IOL implementations Lens 1, Lens 2, Lens 3, Lens 4 and Lens 5. The predicted percentage of spectacle independence using a Bayesian model with multidimensional values as described herein as well as a single through-focus VA at one defocus value is also shown in the table below. The average error and the r^2 values for the different Bayesian models are also included in the table below.

|  | Lens 1 | Lens 2 | Lens 3 | Lens 4 | Lens 5 | Error | r^2 |
|---|---|---|---|---|---|---|---|
| Clinical | 93% | 76% | 66% | 62% | 1% | | |
| Bayesian Model with VA at a plurality of defocus values | 95% | 70% | 74% | 51% | 2% | 5% | 0.96 |
| Bayesian Model with VA at defocus value of −3D only | 87% | 71% | 59% | 36% | 15% | 12% | 0.84 |
| Bayesian Model with VA at defocus value −2.5D only | 71% | 73% | 66% | 38% | 13% | 12% | 0.83 |
| Bayesian Model with VA at defocus value −2D only | 37% | 63% | 69% | 50% | 12% | 19% | 0.45 |
| Bayesian Model with VA at defocus value −1.5D only | 36% | 44% | 60% | 59% | 34% | 26% | 0.07 |

It is noted from the table above that the Bayesian model based on through-focus VA at a plurality of defocus values as described herein had the highest degree of correlation (r^2 of 0.96 with the clinically measured spectacle independence.

Figure 5:
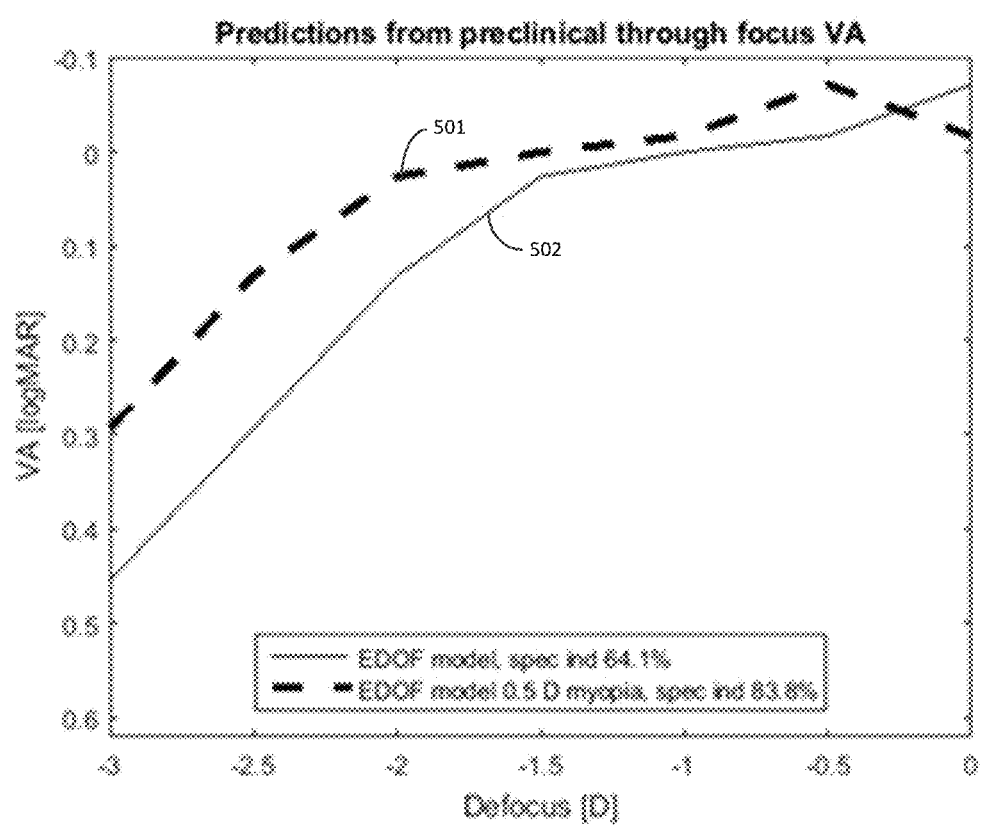
FIG. 5 illustrates the predicted spectacle independence based on pre-clinical data for different implementations of intraocular lenses.

The benefit of inducing 0.5 D of myopia for mini-monovision can also be evaluated using the through focus VA predicted from pre-clinical methods. FIG. 5 shows the through-focus VA based on pre-clinical data for an implementation of an IOL (curve 502) and the same curved shifted by 0.5 D (curve 501). Using the Bayesian model discussed herein, it was estimated that an extended range of vision IOL with a spectacle independence rate of 62% could have that rate increased to 83.2% if the patients were made 0.5 D myopic.

Figure 6:
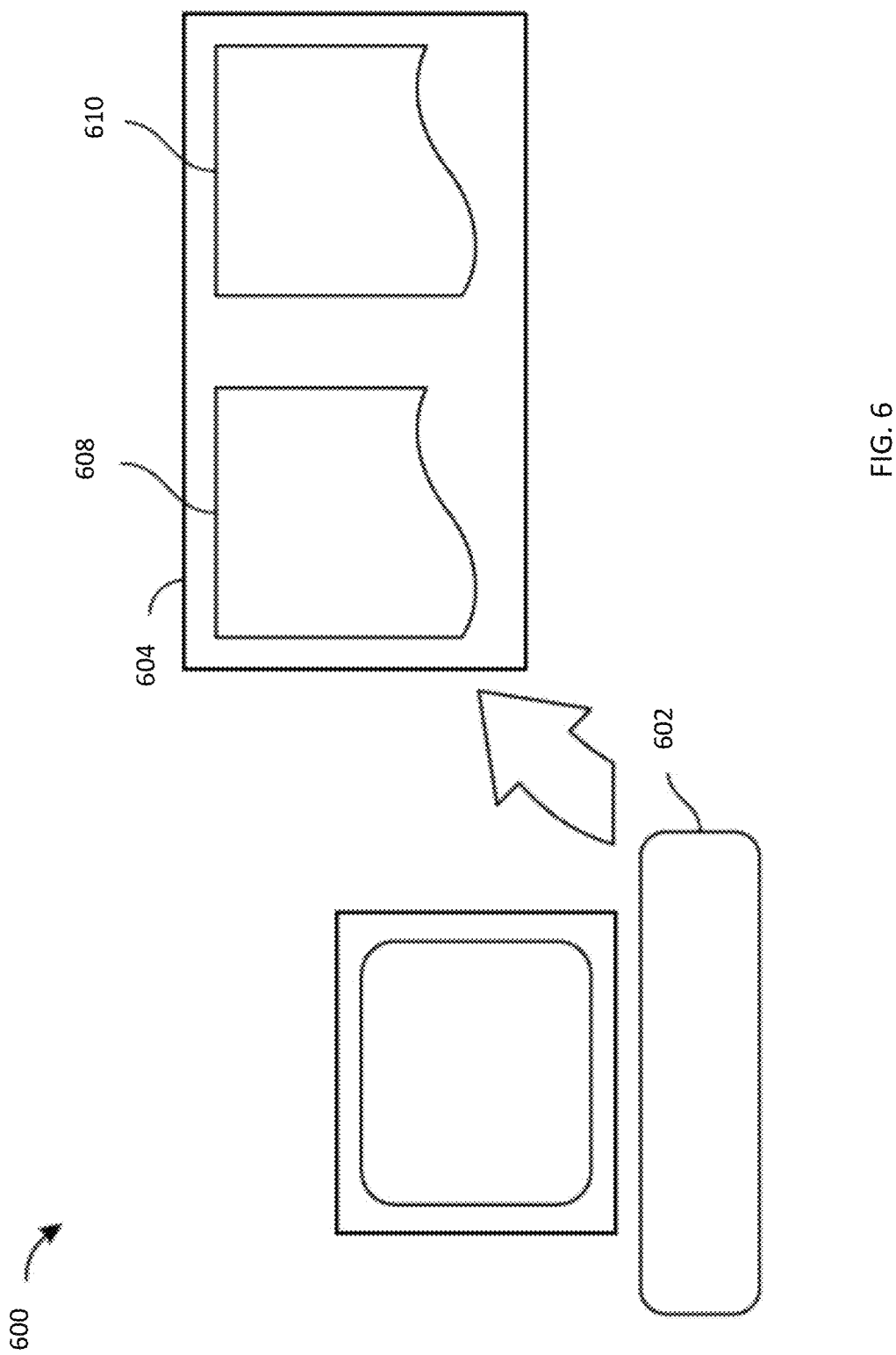
FIG. 6 is a graphical representation of the elements of computing system for designing or selecting an ophthalmic lens.

Referring to FIG. 6, in certain embodiments, a computer system 600 for estimating the probability of being spectacle independent based on available or measured pre-clinical data for an IOL comprises an electronic processor 602 and a computer readable memory 604 coupled to the processor 602. The computer readable memory 604 has stored therein an array of ordered values 608 and sequences of instructions 610 which, when executed by the processor 602, cause the processor 602 to perform certain functions or execute certain modules. For example, a module can be executed that is configured to calculate spectacle independence for one or more IOLs. As another example, a module can be executed that is configured to perform the Bayesian analysis discussed herein and select an IOL that has the highest probability of being spectacle independent. As another example, a module can be executed that is configured to determine an improved or optimal IOL design that improves the probability of being spectacle independent.

The array of ordered values 608 may comprise, for example, one or more ocular dimensions of an eye or plurality of eyes from a database, a desired refractive outcome, parameters of an eye model based on one or more characteristics of at least one eye, and data related to an IOL or set of IOLs such as a power, clinical data providing the number of subjects who are spectacle dependent at one or more VA values, and/or clinical data providing the number of subjects who are spectacle independent at one or more VA values. In some embodiments, the sequence of instructions 610 includes variation of IOL characteristics such as radii of curvature, diffraction power, diffraction step height, transition zones and IOL thickness, using these characteristics in a ray tracing simulation software to predict through-focus VA, using Bayesian analysis to predict the probability of spectacle independence, optimize IOL characteristics to increase spectacle independence or select an IOL having the highest probability of spectacle independence.

The computer system 600 may be a general purpose desktop or laptop computer or may comprise hardware specifically configured performing the desired calculations. In some embodiments, the computer system 600 is configured to be electronically coupled to another device such as a phacoemulsification console or one or more instruments for obtaining measurements of an eye or a plurality of eyes. In other embodiments, the computer system 600 is a handheld device that may be adapted to be electronically coupled to one of the devices just listed. In yet other embodiments, the computer system 600 is, or is part of, refractive planner configured to provide one or more suitable intraocular lenses for implantation based on physical, structural, and/or geometric characteristics of an eye, and based on other characteristics of a patient or patient history, such as the age of a patient, medical history, history of ocular procedures, life preferences, and the like.

In certain embodiments, the system 600 includes or is part a phacoemulsification system, laser treatment system, optical diagnostic instrument (e.g, autorefractor, aberrometer, and/or corneal topographer, or the like). For example, the computer readable memory 604 may additionally contain instructions for controlling the handpiece of a phacoemulsification system or similar surgical system. Additionally or alternatively, the computer readable memory 604 may additionally contain instructions for controlling or exchanging data with an autorefractor, aberrometer, tomographer, and/or topographer, or the like.

Rates of spectacle independence can be predicted from through focus VA. It is better to use a combination of VA at many distances than any one distance. Models based on combining clinical data from many studies can offer greater understanding of potential patient outcomes, such as predicting benefits from mini-monovision using EDOF IOLs.

The above presents a description of the best mode contemplated of carrying out the concepts disclosed herein, and of the manner and process of making and using it, in such full, clear, concise, and exact terms as to enable any person skilled in the art to which it pertains to make and use the concepts described herein. The systems, methods and devices disclosed herein are, however, susceptible to modifications and alternate constructions from that discussed above which are fully equivalent. Consequently, it is not the intention to limit the scope of this disclosure to the particular embodiments disclosed. On the contrary, the intention is to cover modifications and alternate constructions coming within the spirit and scope of the present disclosure as generally expressed by the following claims, which particularly point out and distinctly claim the subject matter of the implementations described herein.

Although embodiments have been described and pictured in an example form with a certain degree of particularity, it should be understood that the present disclosure has been made by way of example, and that numerous changes in the details of construction and combination and arrangement of parts and steps may be made without departing from the spirit and scope of the disclosure as set forth in the claims hereinafter.

As used herein, the term "processor" refers broadly to any suitable device, logical block, module, circuit, or combination of elements for executing instructions. For example, the processor 1002 can include any conventional general purpose single- or multi-chip microprocessor such as a Pentium® processor, a MIPS® processor, a Power PC® processor, AMD® processor, ARM processor, or an ALPHA® processor. In addition, the processor 602 can include any conventional special purpose microprocessor such as a digital signal processor. The various illustrative logical blocks, modules, and circuits described in connection with the embodiments disclosed herein can be implemented or performed with a general purpose processor, a digital signal processor (DSP), an application specific integrated circuit (ASIC), a field programmable gate array (FPGA), or other programmable logic device, discrete gate or transistor logic, discrete hardware components, or any combination thereof designed to perform the functions described herein. Processor 302 can be implemented as a combination of computing devices, e.g., a combination of a DSP and a microprocessor, a plurality of microprocessors, one or more microprocessors in conjunction with a DSP core, or any other such configuration.

Computer readable memory 604 can refer to electronic circuitry that allows information, typically computer or digital data, to be stored and retrieved. Computer readable memory 604 can refer to external devices or systems, for example, disk drives or solid state drives. Computer readable memory 1004 can also refer to fast semiconductor storage (chips), for example, Random Access Memory (RAM) or various forms of Read Only Memory (ROM), which are directly connected to the communication bus or the processor 602. Other types of memory include bubble memory and core memory. Computer readable memory 604 can be physical hardware configured to store information in a non-transitory medium.

Methods and processes described herein may be embodied in, and partially or fully automated via, software code modules executed by one or more general and/or special purpose computers. The word "module" can refer to logic embodied in hardware and/or firmware, or to a collection of software instructions, possibly having entry and exit points, written in a programming language, such as, for example, C or C++. A software module may be compiled and linked into an executable program, installed in a dynamically linked library, or may be written in an interpreted programming language such as, for example, BASIC, Perl, or Python. It will be appreciated that software modules may be callable from other modules or from themselves, and/or may be invoked in response to detected events or interrupts. Software instructions may be embedded in firmware, such as an erasable programmable read-only memory (EPROM). It will be further appreciated that hardware modules may comprise connected logic units, such as gates and flip-flops, and/or may comprised programmable units, such as programmable gate arrays, application specific integrated circuits, and/or processors. The modules described herein can be implemented as software modules, but also may be represented in hardware and/or firmware. Moreover, although in some embodiments a module may be separately compiled, in other embodiments a module may represent a subset of instructions of a separately compiled program, and may not have an interface available to other logical program units.

In certain embodiments, code modules may be implemented and/or stored in any type of computer-readable medium or other computer storage device. In some systems, data (and/or metadata) input to the system, data generated by the system, and/or data used by the system can be stored in any type of computer data repository, such as a relational database and/or flat file system. Any of the systems, methods, and processes described herein may include an interface configured to permit interaction with users, operators, other systems, components, programs, and so forth.

The invention claimed is:

1. An optical system configured to identify an intraocular lens (IOL) that will improve post-surgical spectacle independence, the system comprising a processor configured to execute programmable instructions stored in a non-transitory computer storage medium to:
    calculate, using a ray tracing simulation, predicted pre-clinical visual acuity at a first defocus position for at least two IOLs based on pre-clinical data comprising at least one parameter of an eye model and at least one IOL characteristic of the at least two IOLs, the at least one IOL characteristic selected from the group consisting of refractive index, radii of curvature, diffraction power, diffraction step height, transition zones, and IOL thickness;
    calculate, using Bayesian analysis, a probability of achieving spectacle independence for the at least two IOLs based on the predicted pre-clinical visual acuity and clinical data providing visual acuity at the first defocus position for the at least two IOLs in a population of patients implanted with one of the at least two IOLs; and identify one of the at least two IOLs having a higher probability of achieving spectacle independence, the one of the at least two IOLs comprising the at least one IOL characteristic.

2. The optical system of claim 1, wherein the processor is further configured to calculate the probability of achieving spectacle independence for at least two IOLs based on at least one of:

clinical data providing visual acuity at a second defocus position for the at least two IOLs in the population;

standard deviation of pre-clinical visual acuity for the at least two IOLs at the first or the second defocus positions;

clinical data providing minimum readable print size in mm in the population;

modulation transfer function (MTF) at one or more frequencies at different distances for different pupil sizes; or area under the modulation transfer function at one or more frequencies at different distances for different pupil sizes.

3. The optical system of claim 1 or claim 2, wherein the first defocus position is about −2.5 D corresponding to a distance of about 40 cm, or wherein the second defocus position has a value between about −5 D and about −0.5 D.

4. The optical system of any of claims 1-3, wherein a size of the population is less than about 1000.

5. The optical system of claim 1, wherein the processor is configured to execute programmable instructions stored in a non-transitory computer storage medium to transmit one or more parameters of the identified IOL to a display device or an IOL manufacturing system.

6. A system for predicting post-surgical spectacle independence of one or more IOLs, the system comprising a processor configured to execute programmable instructions stored in a non-transitory computer storage medium to:

calculate, using a ray tracing simulation, predicted pre-clinical visual acuity at one or more defocus positions for the one or more IOLs based on pre-clinical data comprising at least one parameter of an eye model and at least one IOL characteristic of the one or more IOLs, the at least one IOL characteristic selected from the group consisting of refractive index, radii of curvature, diffraction power, diffraction step height, transition zones, and IOL thickness; and calculate, using Bayesian analysis, a probability of achieving spectacle independence for the one or more IOLs based on the predicted pre-clinical visual acuity and clinical data providing visual acuity at the one or more defocus positions for the one or more IOLs in a population of patients implanted with one of the one or more IOLs.

7. The system of claim 6, wherein the processor is further configured to execute programmable instructions stored in a non-transitory computer storage medium to calculate the probability of achieving spectacle independent based on one or more combinations of visual acuity at at least two or more defocus positions for the one or more IOLs in the population.

8. The system of claim 7, wherein the processor is further configured to execute programmable instructions stored in a non-transitory computer storage medium to assign weights to the one or more combinations of visual acuity.

9. The system of claim 8, wherein the weights are determined based on a machine learning algorithm.

* * * * *